(12) United States Patent
Tormo i Blasco et al.

(10) Patent No.: US 7,282,503 B2
(45) Date of Patent: Oct. 16, 2007

(54) FUNGICIDAL MIXTURES BASED ON IMIDAZOLE DERIVATIVES

(75) Inventors: Jordi Tormo i Blasco, Laudenbach (DE); Thomas Grote, Wachenheim (DE); Eberhard Ammermann, Heppenheim (DE); Reinhard Stierl, Freinsheim (DE); Siegfried Strathmann, Limburgerhof (DE); Ulrich Schöfl, Brühl (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 244 days.

(21) Appl. No.: 10/532,769

(22) PCT Filed: Nov. 14, 2003

(86) PCT No.: PCT/EP03/12770

§ 371 (c)(1),
(2), (4) Date: Apr. 27, 2005

(87) PCT Pub. No.: WO2004/045290

PCT Pub. Date: Jun. 3, 2004

(65) Prior Publication Data

US 2006/0100220 A1    May 11, 2006

(30) Foreign Application Priority Data

Nov. 15, 2002  (DE) .................................. 102 53 590

(51) Int. Cl.
*A01N 43/50*   (2006.01)
*A01N 43/76*   (2006.01)
*A01N 43/80*   (2006.01)
*A01N 43/90*   (2006.01)

(52) U.S. Cl. ................. 514/259.31; 514/374; 514/376; 514/378; 514/380; 514/393; 514/394; 514/395; 514/396; 514/397; 514/398; 514/399; 514/400

(58) Field of Classification Search ........... 514/259.31, 514/395, 398
See application file for complete search history.

(56) References Cited

U.S. PATENT DOCUMENTS

| 6,020,354 A | 2/2000 | Assmann et al. |
| 6,268,371 B1 | 7/2001 | Sieverding et al. |
| 6,559,136 B1 | 5/2003 | Mauler-Machnik et al. |
| 2004/0029930 A1 | 2/2004 | Eicken et al. |

FOREIGN PATENT DOCUMENTS

| EP | 0 298 196 A1 | 1/1989 |
| EP | 0 988 790 A1 | 3/2000 |
| WO | WO-98/46607 A1 | 10/1998 |
| WO | WO-98/48628 A1 | 11/1998 |
| WO | WO-02/49435 A1 | 6/2002 |

*Primary Examiner*—John Pak
(74) *Attorney, Agent, or Firm*—Birch, Stewart, Kolasch and Birch, LLP

(57) ABSTRACT

Disclosed are fungicidal mixtures containing a synergistically effective amount of A) a triazolopyrimidine of formula I, and B) imidazole derivatives of formula II, wherein $X^1$ and $X^2$ represent halogen and phenyl which can be substituted by halogen or alkyl, or $X^1$ and $X^2$ form a difluoromethylendioxyphenyl group along with the bridging C═C double bond, $X^3$ represents cyano or halogen, and $X^4$ represents dialkylamino or isoxazol-4yl that can carry two alkyl radicals. The invention also relates to methods for controlling destructive fungi by means of mixtures of compounds I and II, agents containing said mixtures, and the use of compounds I and II for producing such mixtures.

11 Claims, No Drawings

FUNGICIDAL MIXTURES BASED ON IMIDAZOLE DERIVATIVES

This application is a 371 of PCT/EP03/12770, filed on 11/14/2003.

The present invention relates to fungicidal mixtures, comprising

A) the triazolopyrimidine of the formula I

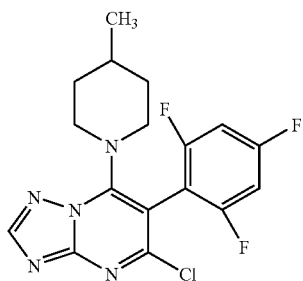

B) imidazole derivatives of the formula II

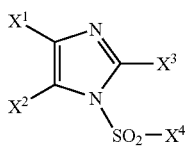

where $X^1$ and $X^2$ are halogen and phenyl which may be substituted by halogen or $C_1$-$C_4$-alkyl or $X^1$ and $X^2$ together with the bridging C=C double bond form a 3,4-difluoromethylendioxyphenyl group;

$X^3$ is cyano or halogen, and $X^4$ is di-($C_1$-$C_4$-alkyl)amino or isoxazol-4-yl which may carry two $C_1$-$C_4$-alkyl radicals, in a synergistically effective amount.

Moreover, the invention relates to methods for controlling phytopathogenic harmful fungi using mixtures of the compounds I and II, to compositions comprising these mixtures and to the use of the compounds I and II for preparing such mixtures.

The compound of the formula 1,5-chloro-7-(4-methyl-pipiridin-1-yl)-6-(2,4,6-trifluorophenyl)-[1,2,4]triazolo[1,5-a]pyrimidine, its preparation and its action against harmful fungi are known from the literature (WO 98/46607).

Mixtures of triazolopyrimidines of the formula I with other active compounds are known from EP-A 988 790 and U.S. Pat. No. 6,268,371.

Also known are the imidazole derivatives of the formula II, their preparation and their action against harmful fungi (EP-A 298 196, WO 97/06171).

Mixtures of the imidazole derivatives of the formula II with other active compounds are known from WO 98/48628 and WO 00/30440.

To reduce the risk of selection of resistant fungus strains, it is nowadays customary to use mixtures of different active compounds for controlling harmful fungi. By combining active compounds having different mechanisms of action, it is possible to ensure successful control over a relatively long period of time.

It is an object of the present invention to provide further particularly effective mixtures for controlling harmful fungi and in particular for certain indications.

With a view to effective resistance management and reducing the application rates and to improving the activity spectrum of the known compounds I and II, it was an object of the present invention to provide mixtures which, with the total amount of active compounds applied being reduced, have improved action against harmful fungi (synergistic mixtures).

We have found that this object is achieved by the mixtures defined at the outset. Moreover, it has been found that simultaneous, that is joint or separate, application of the compounds I and the compounds II or successive application of the compounds I and the compounds II allows better control of harmful fungi than is possible with the individual compounds alone.

The mixtures according to the invention have synergistic action and are therefore particularly suitable for controlling harmful fungi and in particular powdery and downy mildew fungi in cereals, vegetables, fruit, ornamental plants and grapevines.

The mixtures according to the invention preferably comprise, as active components, the compound of the formula I and a compound of the formula II.

Preference is given to compounds of the formula II in which $X^1$ is halogen, in particular chlorine, and $X^2$ is tolyl, in particular p-tolyl.

Preference is likewise given to compounds of the formula II, in which $X^4$ is dimethylamino.

In addition, particular preference is given to the compound of the formula IIa (common name: cyazofamid). This compound is known from EP-A 298 196.

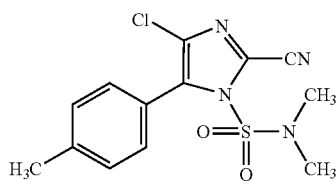

Preference is furthermore given to compounds of the formula II in which $X^1$ and $X^2$ together with the bridging C=C double bond form a 3,4-difluoromethylendioxyphenyl group.

In addition, preference is given to compounds of the formula II in which $X^4$ is 3,5-dimethylisoxazol-4-yl.

Particular preference is given to compounds of the formula IIb in which Y is halogen.

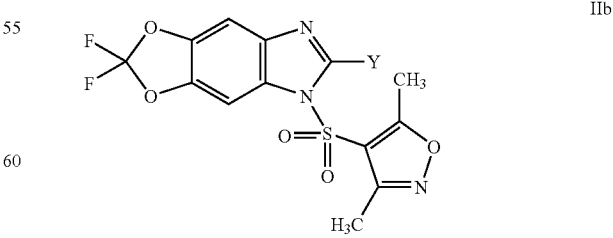

Halogen denotes fluorine, chlorine, bromine and iodine. Particular preference is given to compounds of the formula IIb in which Y is bromine (IIb-1) or chlorine (IIb-2).

For use in mixtures with the triazolopyrimidine of the formula I, preference is given to compound IIa.

Owing to the basic character of their nitrogen atoms, the compounds I and II are capable of forming salts or adducts with inorganic or organic acids or with metal ions.

Examples of inorganic acids are hydrohalic acids such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or -diphosphonic acids (aromatic radicals, such as phenyl and naphthyl, which carry one or two phosphonic acid radicals), where the alkyl and aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth subgroup, in particular chromium, manganese, iron, cobalt, nickel, copper, zinc, and furthermore of the second main group, in particular calcium and magnesium, and of the third and fourth main group, in particular aluminum, tin and lead. The metals can exist in the various valencies which they can assume.

The ratio of the compounds I and II can be varied within wide ranges; preferably, the active compounds are employed in a weight ratio in the range from 50:1 to 1:50, preferably from 20:1 to 1:20, in particular from 10:1 to 1:10.

When preparing the mixtures, it is preferred to employ the pure active compounds I and II, to which further active compounds against harmful fungi or other pests, such as insects, arachnids or nematodes, or else herbicidal or growth-regulating active ingredients or fertilizers can be added.

The mixtures of the compounds I and II, or the compounds I and II used simultaneously, together or separately, exhibit outstanding activity against a wide range of phytopathogenic fungi, in articular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants, such as cotton, vegetable species (for example cucumbers, beans, tomatoes, potatoes and cucurbits), barley, grass, oats, bananas, coffee, corn, fruit species, rice, rye, soybean, grapevine, wheat, ornamentals, sugar cane, and a multiplicity of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* in apples, *Bipolaris* and *Drechslera* species in cereals, rice and lawns, *Septoria nodorum* in wheat, *Botrytis cinera* in strawberries, vegetables, ornamentals and grapevines, *Mycosphaerella* species in bananas, groundnuts and cereals, *Pseudocercosporella herpotrichoides* in wheat and barley, *Pyricularia oryzae* in rice, *Phytophthora infestans* in potatoes and tomatoes, *Pseudoperonospora* species in cucurbits and hops, *Plasmopara viticola* in grapevines, *Alternaria* species in vegetables and fruit and also *Fusarium* and *Verticillium* species.

Moreover, they can be used in the protection of materials (for example the protection of wood), for example against *Paecilomyces variotii*.

The compounds I and II can be applied simultaneously, that is either together or separately, or in succession, the sequence, in the case of separate application, generally not having any effect on the result of the control measures.

Depending on the kind of effect desired, the application rates of the mixtures according to the invention are, in particular in agricultural crop areas, from 0.01 to 2 kg/ha, preferably from 0.05 to 1.5 kg/ha, in particular from 0.05 to 0.75 kg/ha.

The application rates of the compounds I are from 10 g/ha to 1 000 kg/ha, preferably from 20 to 750 kg/ha, in particular from 20 to 500 kg/ha.

Correspondingly, in the case of the compounds II, the application rates are from 5 g/ha to 500 g/ha, preferably from 50 to 500 g/ha, in particular from 50 to 200 g/ha.

For seed treatment, the application rates of the mixture are generally from 0.001 to 1 g/kg of seed, preferably from 0.01 to 0.5 g/kg, in particular from 0.01 to 0.1 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The mixtures according to the invention, or the compounds I and II, can be converted into the customary formulations, for example solutions, emulsions, suspensions, dusts, powders, pastes and granules. The use form depends on the respective intended purpose; in each case, it should ensure a fine and uniform distribution of the mixture according to the invention.

The formulations are prepared in a known manner, e.g. by extending the active compound with solvents and/or carriers, if desired using emulsifiers and dispersants. Suitable solvents/auxiliaries for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristerylphenyl polyglycol ether, alkylaryl polyether alcohols, alcohol/- and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Powders, compositions for broadcasting and dusts can be prepared by mixing or jointly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic minerals, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compounds. The active compounds are employed in a purity of from 90% to 100%, preferably from 95% to 100% (according to NMR spectrum).

The following are examples of formulations:

1. Products for dilution with water

A) Water-Soluble Concentrates (SL)
   10 parts by weight of the active compounds are dissolved in water or in a water-soluble solvent. As an alternative, wetters or other auxiliaries are added. The active compound dissolves upon dilution with water.

B) Dispersible Concentrates (DC)
   20 parts by weight of the active compounds are dissolved in cyclohexanone with addition of a dispersant, for example polyvinylpyrrolidone. Dilution with water gives a dispersion.

C) Emulsifiable Concentrates (EC)
   15 parts by weight of the active compounds are dissolved in xylene with addition of calcium dodecylbenzenesulfonate and castor oil ethoxylate (in each case 5%). Dilution with water gives an emulsion.

D) Emulsions (EW, EO)
   40 parts by weight of the active compounds are dissolved in xylene with addition of calcium dodecylbenzenesulfonate and castor oil ethoxylate (in each case 5%). This mixture is introduced into water by means of an emulsifier (Ultraturax) and made into a homogeneous emulsion. Dilution with water gives an emulsion.

E) Suspensions (SC, OD)
   In an agitated ball mill, 20 parts by weight of the active compounds are comminuted with addition of dispersant, wetters and water or an organic solvent to give a fine active compound suspension. Dilution with water gives a stable suspension of the active compound.

F) Water-Dispersible Granules and Water-Soluble Granules (WG, SG)
   50 parts by weight of the active compounds are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)
   75 parts by weight of the active compounds are ground in a rotor-stator mill with addition of dispersants, wetters and silica gel. Dilution with water gives a stable dispersion or solution of the active compound.

2. Products to be Applied Undiluted

H) Dustable Powders (DP)
   5 parts by weight of the active compounds are ground finely and mixed intimately with 95% of finely divided kaolin. This gives a dustable product.

I) Granules (GR, FG, GG, MG)
   0.5 part by weight of the active compounds is ground finely and associated with 95.5% carriers. Current methods are extrusion, spray-drying or fluidized bed. This gives granules to be applied undiluted.

J) ULV Solutions (UL)
   10 parts by weight of the active compounds are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dust compositions, compositions for broadcasting, or granules, by means of spraying, atomizing, dusting, broadcasting or pouring. The use forms depend entirely on the intended purposes; it is intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates suitable for dilution with water composed of active substance, wetter, tackifier, dispersant or emulsifier and, if appropriate, solvent or oil.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), where it is possible to apply formulations comprising over 95% by weight of active compound, or even to apply the active compound without additives.

Oils of various type, wetters, adjuvants, herbicides, fungicides, other pesticides, or bactericides may be added to the active compounds, if appropriate just immediately prior to use (tank mix). These agents can be admixed with the agents according to the invention in a weight ratio of 1:10 to 10:1.

USE EXAMPLES

The synergistic activity of the mixtures according to the invention can be demonstrated by the following experiments:

The active compounds, separately or together, were prepared as a stock solution with 0.25% by weight of active compound in acetone or DMSO. 1% by weight of the emulsifier Uniperol® EL (wetting agent having emulsifying and dispersing action based on ethoxylated alkylphenols) was added to this solution, and the solution was diluted with water to the desired concentration.

Evaluation is carried out by determining the infected leaf areas as a percentage. These percentages are converted into efficacies. The efficacy (W) is calculated as follows using Abbot's formula:

$$W=(1-\alpha/\beta)\cdot 100$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected. The expected efficacies of the mixtures of the active compounds are determined using Colby's formula [R. S. Colby, Weeds 15, 20-22 (1967)] and compared with the observed efficacies.

$$\text{Colby's formula: } E=x+y-x\cdot y/100$$

E expected efficacy, expressed as a % of the untreated control, when using the mixture of the active compounds A and B at the concentrations a and b x efficacy, expressed as a % of the untreated control, when using active compound A at a concentration a y efficacy, expressed as a % of the untreated control, when using active compound B at a concentration b Example 1

Activity Against *peronospora* of Vines Caused by *Plasmopara viticola*

Leaves of potted vines of the cultivar "Müller-Thurgau" were sprayed to runoff point with an aqueous suspension having the concentration of active compounds stated below. The next day, the undersides of the leaves were inoculated with an aqueous zoospore suspension of *Plasmopara viticola*. The vines were then initially placed in a water-vapor-saturated chamber at 24° C. for 48 hours and then in a greenhouse at 20-30° C. for 5 days. After this period of time, the plants were again placed in a moist chamber for 16 hours to promote sporangiophore eruption. The extent to which the infection had developed on the undersides of the leaves was then determined visually.

TABLE A individual active compounds

| Experiment No. | Active compound | Concentration of active compound in the spray liquor [ppm] | Efficacy in % of the untreated control |
|---|---|---|---|
| 1 | Control (untreated) | (88% infection) | 0 |
| 2 | I | 7.5 | 32 |
|   |   | 3.75 | 9 |
| 3 | IIa (cyazofamid) | 6 | 83 |
|   |   | 3 | 72 |
| 4 | IIb-1 | 6 | 9 |
|   |   | 3 | 9 |
|   |   | 0.75 | 0 |
|   |   | 0.375 | 0 |

TABLE B mixtures according to the invention

| Experiment No. | Mixture of active compounds Concentration Mixing ratio | Observed efficacy | Calculated efficacy* |
|---|---|---|---|
| 5 | I + IIa 7.5 + 6 ppm 1.25:1 | 100 | 88 |
| 6 | I + IIa 3.75 + 3 ppm 1.25:1 | 97 | 74 |
| 7 | I + IIa 3.75 + 6 ppm 1:1.6 | 97 | 85 |
| 8 | I + IIb-1 7.5 + 0.75 ppm 10:1 | 66 | 32 |
| 9 | I + IIb-1 3.75 + 0.375 ppm 10:1 | 32 | 9 |
| 10 | I + IIb-1 7.5 + 6 ppm 1.25:1 | 77 | 38 |
| 11 | I + IIb-1 3.75 + 3 ppm 1.25:1 | 66 | 17 |
| 12 | I + IIb-1 3.75 + 6 ppm 1:1.6 | 55 | 17 |

*)efficacy calculated using Colby's formula

Example 2

Activity Against Late Blight of Tomato Caused by *Phytophthora infestans*

Leaves of potted plants of the cultivar "Große Fleischtomate St. Pierre" were sprayed to runoff point with an aqueous suspension having the concentration of active compound stated below. The next day, the leaves were infected with a cold aqueous zoospore suspension of *Phytophthora infestans* having a density of 0.25×10⁶ spores/ml. The plants were then placed in a water-vapor-saturated chamber at 18-20° C. After 6 days, the late blight on the untreated, but infected control plants had developed to such an extent that the infection could be determined visually in %.

TABLE C individual active compounds

| Experiment No. | Active compound | Concentration of active compound in the spray liquid [ppm] | Efficacy in % of the untreated control |
|---|---|---|---|
| 13 | Control (untreated) | (90% infection) | 0 |
| 14 | I | 30 | 33 |
|  |  | 15 | 0 |
|  |  | 7.5 | 0 |
|  |  | 3.75 | 0 |
| 15 | IIa (cyazofamid) | 6 | 89 |
|  |  | 3 | 78 |
|  |  | 1.5 | 67 |
|  |  | 0.75 | 56 |
| 16 | IIb-1 | 6 | 83 |
|  |  | 3 | 44 |
|  |  | 0.75 | 0 |
|  |  | 0.375 | 0 |

TABLE D combinations according to the invention

| Experiment No. | Mixture of active compounds Concentration Mixing ratio | Observed efficacy | Calculated efficacy*) |
|---|---|---|---|
| 17 | I + IIa<br>30 + 3 ppm<br>10:1 | 99 | 85 |
| 18 | I + IIa<br>15 + 1.5 ppm<br>10:1 | 94 | 67 |
| 19 | I + IIa<br>3.75 + 3 ppm<br>1.25:1 | 99 | 78 |
| 20 | I + IIa<br>3.75 + 6 ppm<br>1:1.6 | 100 | 89 |
| 21 | I + IIb-1<br>7.5 + 0.75 ppm<br>10:1 | 44 | 0 |
| 22 | I + IIb-1<br>3.75 + 0.375 ppm<br>10:1 | 56 | 0 |
| 23 | I + IIb-1<br>3.75 + 3 ppm<br>1.25:1 | 61 | 44 |
| 24 | I + IIb-1<br>3.75 + 6 ppm<br>1:1.6 | 94 | 83 |

*)efficacy calculated using Colby's formula

The test results show that for all mixing ratios the observed efficacy of the mixtures according to the invention is considerably higher than that predicted using Colby's formula.

We claim:

1. A fungicidal mixture, comprising
A) the triazolopyrimidine of the formula I

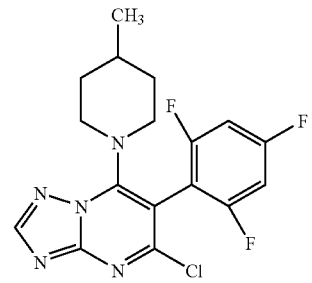

and
B) an imidazole derivative of the formula II

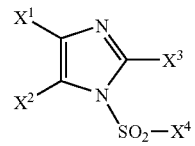

where $X^1$ and $X^2$ are halogen and phenyl, respectively, wherein phenyl may be substituted by halogen or $C_1$-$C_4$-alkyl or $X^1$ and $X^2$ together with the bridging C═C double bond form a 3,4-difluoromethylendioxyphenyl group;

$X^3$ is cyano or halogen, and $X^4$ is di-($C_1$-$C_4$-alkyl)amino or isoxazol-4-yl which may carry two $C_1$-$C_4$-alkyl radicals, in a synergistically effective amount.

2. A fungicidal mixture as claimed in claim 1, comprising, as the imidazole derivative, the compound IIa

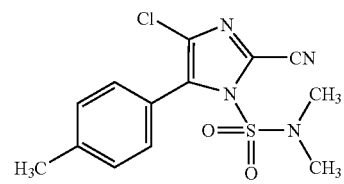

3. A fungicidal mixture as claimed in claim 1, comprising, as the imidazole derivative, a compound of the formula IIb,

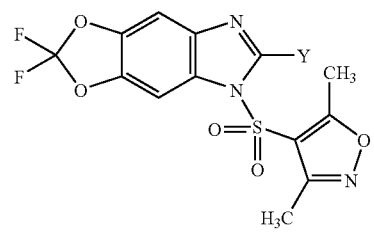

wherein Y is halogen.

4. A fungicidal mixture as claimed in any one of claims 1 to 3, wherein the weight ratio of the triazolopyrimidine of the formula I to the imidazole derivative of the formula II is from 50:1 to 1:50.

5. A fungicidal composition, comprising the fungicidal mixture as claimed in claim 1 and a solid or liquid carrier.

6. A method for controlling phytopathogenic harmful fungi, which comprises treating the harmful fungi, their habitat or the plants, seeds, soils, areas, materials or spaces to be kept free from them with the triazolopyrimidine of the formula I as set forth in claim 1 and an imidazole derivative of the formula II as set forth in claim 1.

7. A method as claimed in claim 6, wherein the triazolopyrimidine of the formula I and an imidazole derivative of the formula II are applied simultaneously, that is either together or separately, or in succession.

8. A method as claimed in claim 6, wherein the triazolopyrimidine of the formula I is applied in an amount of from 0.01 to 2.5 kg/ha.

9. A method as claimed in claim 6, wherein the imidazole derivative of the formula II is applied in an amount of from 5 g/ha to 500 g/ha.

10. A fungicidal mixture as claimed in any one of claims 1 to 3, wherein the weight ratio of the triazolopyrimidine of the formula I to the imidazole derivative of the formula II is from 20:1 to 1:20.

11. A fungicidal mixture as claimed in any one of claims 1 to 3, wherein the weight ratio of the triazolopyrimidine of the formula I to the imidazole derivative of the formula II is from 10:1 to 1:10.

* * * * *